(12) United States Patent
Coumans et al.

(10) Patent No.: US 7,764,821 B2
(45) Date of Patent: Jul. 27, 2010

(54) METHODS AND ALGORITHMS FOR CELL ENUMERATION IN A LOW-COST CYTOMETER

(75) Inventors: Frank A. W. Coumans, GD Stein (NL); Jan Greve, Oldenzaal (NL); Frank P. Modica, Princeton, NJ (US); Leon W. M. M. Terstappen, Amsterdam (NL); Arjan G. J. Tibbe, Deventer (NL); John A. Verrant, Solebury, PA (US)

(73) Assignee: Veridex, LLC, Raritan, NJ (US)

( * ) Notice: Subject to any disclaimer, the term of this patent is extended or adjusted under 35 U.S.C. 154(b) by 851 days.

(21) Appl. No.: 11/434,321

(22) Filed: May 12, 2006

(65) Prior Publication Data
US 2007/0117158 A1     May 24, 2007

Related U.S. Application Data

(63) Continuation-in-part of application No. 10/903,798, filed on Jul. 30, 2004.

(60) Provisional application No. 60/781,661, filed on Mar. 13, 2006, provisional application No. 60/729,536, filed on Oct. 24, 2005.

(51) Int. Cl.
  *G06K 9/00* (2006.01)
(52) U.S. Cl. .................................. 382/133; 382/128
(58) Field of Classification Search ......... 382/128–133, 382/145, 149; 435/7.2, 29, 39; 356/73, 121; 250/461.2
  See application file for complete search history.

(56) References Cited

U.S. PATENT DOCUMENTS

| | | | |
|---|---|---|---|
| 5,018,209 A | 5/1991 | Bacus | |
| 5,073,857 A | 12/1991 | Peters et al. | |
| 5,186,827 A | 2/1993 | Liberti et al. | |
| 5,287,272 A | 2/1994 | Rutenberg et al. | |

(Continued)

FOREIGN PATENT DOCUMENTS

WO     9908233     2/1999

(Continued)

*Primary Examiner*—Duy M Dang
(74) *Attorney, Agent, or Firm*—Johnson & Johnson; Joseph F. Aceto, Esq.

(57) ABSTRACT

The enumeration of cells in fluids by flow cytometry is widely used across many disciplines such as assessment of leukocyte subsets in different bodily fluids or of bacterial contamination in environmental samples, food products and bodily fluids. For many applications the cost, size and complexity of the instruments prevents wider use, for example, CD4 analysis in HIV monitoring in resource-poor countries. The novel device, methods and algorithms disclosed herein largely overcome these limitations. Briefly, all cells in a biological sample are fluorescently labeled, but only the target cells are also magnetically labeled. In addition, non-magnetically labeled cells are imaged for viability in a modified slide configuration. The labeled sample, in a chamber or cuvet, is placed between two wedge-shaped magnets to selectively move the magnetically labeled cells to the observation surface of the cuvet. An LED illuminates the cells and a CCD camera captures the images of the fluorescent light emitted by the target cells. Image analysis performed with a novel algorithm provides a count of the cells on the surface that can be related to the target cell concentration of the original sample. The compact cytometer system provides a rugged, affordable and easy-to-use technique, which can be used in remote locations.

7 Claims, 6 Drawing Sheets

U.S. PATENT DOCUMENTS

| | | | |
|---|---|---|---|
| 5,340,749 A * | 8/1994 | Fujiwara et al. | ............... 435/29 |
| 5,466,574 A | 11/1995 | Liberti et al. | |
| 5,556,764 A | 9/1996 | Sizto et al. | |
| 5,579,531 A | 11/1996 | Sugita | |
| 5,665,582 A | 9/1997 | Kausch et al. | |
| 5,698,271 A | 12/1997 | Liberti et al. | |
| 5,766,944 A | 6/1998 | Ruiz | |
| 5,789,152 A | 8/1998 | Black et al. | |
| 5,985,153 A | 11/1999 | Dolan | |
| 6,097,485 A | 8/2000 | Lievan | |
| 6,136,182 A | 10/2000 | Dolan | |
| 6,221,607 B1 | 4/2001 | Tsipouras et al. | |
| 6,251,615 B1 | 6/2001 | Oberhardt | |
| 6,365,362 B1 | 4/2002 | Terstappen et al. | |
| 6,418,236 B1 | 7/2002 | Ellis et al. | |
| 6,620,591 B1 | 9/2003 | Dunlay et al. | |
| 6,682,940 B2 | 1/2004 | Pankowsky | |
| 6,890,426 B2 | 5/2005 | Terstappen | |
| 6,893,881 B1 | 5/2005 | Fodstad et al. | |
| 6,967,328 B2 * | 11/2005 | Kienzle et al. | .............. 382/149 |
| 7,011,794 B2 | 3/2006 | Kagan et al. | |
| 2004/0023222 A1 | 2/2004 | Russell et al. | |
| 2006/0024756 A1 | 2/2006 | Tibbe et al. | |

FOREIGN PATENT DOCUMENTS

| | | |
|---|---|---|
| WO | 00045169 | 8/2000 |
| WO | 02065103 | 8/2002 |
| WO | 2005008225 | 1/2005 |
| WO | 2005008226 | 1/2005 |
| WO | 2005005259 | 6/2005 |
| WO | 2005059549 | 6/2005 |
| WO | 2005062059 | 7/2005 |
| WO | 2005095925 | 10/2005 |
| WO | 2006014056 | 2/2006 |

* cited by examiner

A

B

METHODS AND ALGORITHMS FOR CELL ENUMERATION IN A LOW-COST CYTOMETER

CROSS REFERENCE TO RELATED APPLICATIONS

This application is a non-provisional application, which is incorporated by reference herein and claims priority, in part, of U.S. Provisional Application No. 60/357,170, filed 14 Feb. 2002, now abandoned, U.S. Provisional Application Nos. 60/781,661, filed on Mar. 13, 2006 and 60/729,536; filed on Oct. 24, 2006, and is a continuation-in-part of U.S. Ser. No. 10/903,798, filed Feb. 14, 2003.

FIELD OF THE INVENTION

This invention relates generally to simple and low cost electronic optical devices, methods and algorithms for enumeration of microscopic particles distributed in a two-dimensional plane. The novel counting techniques are particularly applicable to enumerating magnetically selected fluorescent cells in complex biological specimens such as blood by means of an inexpensive cell cytometer. Further, the present invention is applicable in the analysis of specific sample characteristics such as, but not limited to, cell viability, leukocyte depletion, and CD4 positive cell counting.

BACKGROUND OF THE INVENTION

The enumeration of absolute levels of cells and their subsets in body fluids is of primary importance in determining the state of health of human beings and mammals in general. The primary analytical platform for performing such analyses is flow cytometry in which the specimen is either injected directly or after prior enrichment in rare cell analysis. Flow cytometry and similar complex analytical systems remain largely inaccessible for routine clinical use in resource-poor countries due to high instrument and reagents costs, lack of technical support, lack of robustness requiring frequent service, and the need for AC power. There is a clear need for simpler, more compact and less expensive systems also operable with emergency DC battery power and preferably exhibiting comparable performance characteristics.

In addition to the above-cited full sized flow cytometry systems available from Becton Dickinson and Beckman-Coulter, these vendors also sell scaled down less expensive versions, which still suffer from the other cited limitations. Similar limitations apply to the compact CyFlow® from Partec GmbH, (Munster, Germany) and to the Guava Personal Cytometer (Burlingame, Calif.). U.S. Pat. No. 6,097,485 (assigned to Integrated Wave Guides, Brookings, S.Dak.) discloses an ultra-miniature personal flow cytometer (pFCM) claimed to be of lower cost, but still exhibiting rather complex, electronic circuitry, optical designs, data reduction, all of which contribute to unacceptable complexity for a third world setting. All these systems use the flow concept, which obviously complicates the instrumental design. These scaled down versions of flow cytometry systems do not meet the clear need for a truly simple, compact, rugged, battery-operable and affordable cell analyzer.

Among the numerous clinical applications for a simple cell analyzer, counting of CD4 cells in HIV, granulocytes and platelets in patients treated with chemotherapy, and leukocytes in blood bags are most important. The current systems and methods for cell analysis have some significant disadvantages. They generally require sophisticated techniques, which involve the use of instruments that are expensive both in terms of initial cost and maintenance as well as requiring highly trained personnel. This makes the conventional systems unsuitable for use in laboratories of resource-poor countries. Therefore, a low-cost, easy-to-use method, for example, for CD4 cell enumeration is needed. Such a method may serve as a compact alternative to the current cell analysis systems that would be suitable for physician practices, bedside testing, or in open field settings with the ability to count rare cells in each condition. Further enumerating white cells in, for example, blood bags by a rapid, inexpensive means, instead of using flow cytometry where the analysis time is very long.

The invention described herein meets the criteria above. The invention uses a CCD camera to image samples. Object detection algorithms are performed on the captured image to count the number of target entities present in a sample.

The prior art contains many computer-assisted microscopes. U.S. Pat. No. 5,018,209 teaches a computer driven microscope in which the user manually selects positive events while looking at an image. Obviously, this does not have a high enough throughput to be an effective analyzer, especially in remote settings.

In U.S. Pat. No. 5,287,272, an automated cytological specimen classification system and method is described. This system relies on a complicated neural network to process images of cells based on morphology. While very effective for classifying objects in images, it requires a large amount of computational resources. Furthermore, human input and subsequent analysis is still necessary. Other devices, such as those described in U.S. Pat. Nos. 5,073,857 and 5,077,806, use window sub-image pixel counting algorithms for image analysis by using predetermined thresholds.

Another set of instruments in the prior art is designed as bench top analyzers. In U.S. Pat. No. 5,073,857, pap smears are analyzed by a computer controlled microscope and camera and computer driven image analysis. In U.S. Pat. No. 6,221,607, an automated microscope is described for analyzing in situ hybridization events in a biological specimen.

The devices in the aforementioned prior art are designed to image slides. None are capable of detecting and enumerating a target population within a biological specimen as defined herein. Furthermore, none appear to be portable or high throughput devices. These instruments are designed to rely on a desktop computer to control the microscope and camera, and to perform image analysis algorithms. The present invention overcomes many of the difficulties that lie in the prior art.

SUMMARY OF THE INVENTION

This invention (sometimes referred to herein by its project name, "EasyCount") describes compact electronic optical instruments, analytical methods, image acquisition, and data reduction algorithms for the detection and enumeration of magnetically labeled target cells or particles. Using whole blood as an example, blood cells are fluorescently labeled using one or more target specific fluorescent dyes, such as a DNA staining dye. The cells of interest or target cells in the blood sample are labeled by incubation with monoclonal antibodies conjugated to ferromagnetic particles. The sample is then placed into an appropriate optical detection chamber or cuvet, which in turn is placed into a magnetic field gradient that selectively causes the magnetically labeled cells to move towards the upper observation surface of the chamber. The target cells are collected and immobilized substantially uniformly on the optically transparent surface of the chamber. A segment of this surface and the labeled target cells thereon are illuminated by means of one or more LED (light emitting diodes). Subsequently, the light emitted by individual target cells is captured by a CCD (charge coupled device).

The present invention provides detection means that incorporate illumination components, filter apparatus, focusing device, software and image analysis that together provide an improved device and methods for low cost, compact electronic optical instrument.

One embodiment of the present invention, called the MagNest configuration, incorporates the magnetic manipulation of labeled cells from a sample wherein the target cells are positioned along the upper glass observation surface of a sample chamber as previously described in U.S. application Ser. No. 10/903,798 and U.S. Pat. Nos. 6,890,426 and 7,011,794. The system counts the number of cells present on the observation surface of a defined area. Since the height of the chamber and area of the observation region are known, the volume from which the cells are extracted can be determined and the number of cells present at the observation surface can be directly converted to the absolute number of cells in the sample.

Application of the Magnest configuration is useful in assessing leukodepletion of a blood sample (60/781,661). Leukocytes are labeled with CD45-PE and captured with CD45 linked to magnetic particles (U.S. Pat. No. 6,365,362). With the complete capture of all CD45 positive cells, a complete quantitative analysis is determined for the leukocytes present in the sample.

Another embodiment of the present invention incorporates the use of a slide configuration whereby a slide enclosed with a cover slip having only an inlet and outlet port is positioned on the viewing stage of the cytometer so as to position all cells along a single viewing plain. The slide configuration is especially applicable in assessing cell viability. A biological sample is assessed for viability by labeling both viable and dead cells. Accordingly, all cells are labeled with acrine orange, Thioflavin T, or any fluorescent agent known in the art to label live cells, for example on the membrane surface or nucleus. Dead cells are labeled with ethidium bromide or any fluorescent agent known in the art.

Table I shows the two configurations and their preferred use. Also, the suggested excitation and emission wavelengths are shown. Wavelengths are chosen to optimize the separation between the excitation and emission spectrum (Stoke shift) of the fluorescent dyes. The wavelengths chosen in Table I are only representative of all possible excitation/emission combination.

TABLE I

|  |  | Viability Assement | Leuko-Depletion | CD-4 Detection |
|---|---|---|---|---|
| Sample | MagNest |  | X | X |
|  | Slide | X |  | X |
| Excitation | 470 nm | X | X | X |
|  | 515 nm |  | X | X |
|  | 530 nm | X |  |  |
|  | 290 nm |  | X | X |
| Emission | 530/540 nm | X |  |  |
|  | 580/550 nm |  | X | X |
|  | 640 nm | X | X | X |
| Magnification | 5× | X | X | X |
|  | 10× |  |  |  |

The cells are counted based on their fluorescence intensity difference with the background. The optimal target cell concentration after sample preparation is between $10^3$ and $10^7$ per milliliter. The emitted fluorescence is imaged onto a CCD camera. Image analysis routines coded inside the system determine the number of cells present, and then the number of cells per unit volume is calculated. The development of the algorithms for image acquisition and data reduction required considerable laborious experimentation and optimization. This resulted in the present invention configuration that exhibits the excellent performance characteristics as described herein.

Further advantages provided by this invention are the functional simplicity in design, ruggedness, compactness, AC or DC power options, and substantially lower purchase and operating costs relative to conventional commercial devices with comparable performance characteristics. The features and improvements of the devices of this invention, exemplified as compact clinical cell cytometer, make them particularly useful for operation in primitive laboratories or under field conditions prevalent in resource-poor countries.

A further improvement is in the individual illumination/light capture components of the cytometer. The LEDs are positioned to illuminate along the long axis of the cartridge at a mean angle of incidence of 45 degrees. The turret provides up to four wavelengths, depending on the intensity required to illuminate the specimen. The present configuration is for two different wavelengths. This ensures maximum illumination and light capture. The use of solid state illumination devices ensures that the light source will outlive the life of the instrument, providing a distinct advantage in field use. The filter changer operates through a slider crank having an eccentric bearing to align the individual filters. The slider crank is optimized for a small space and minimal expense. The preferred number of emission filters is two, but multiple filters are contemplated with the present application.

A further improvement is the elimination of an active Z-stage adjustment when imaging the target cells. Target cells are maintained in focus along the Z-plain with the incorporation of a spring loaded mechanism on the holding device that references the slide or cartridge against the position tabs (monuments) that maintains a fixed distance between the cells and objective lens. The spring support acts to apply a upward force to the cartridge/sample holder when positioned onto the holder. Accordingly, monuments come down onto the sample holder that push against the springs and force the sample to be in a pre-set plane. This eliminates variations in tolerances in the sample holder and cartridge. Thus, any need for changes in focus are eliminated along the Z-direction. A similar principle is used with the slide configuration.

It is to be understood and appreciated that these discoveries, in accordance with the invention, are only illustrative of the many additional potential applications of the apparatus, methods and algorithms that may be envisioned by one of ordinary skill in the art, and thus are not in any way intended to be limiting of the scope of the invention. Accordingly, other objects and advantages of the invention will be apparent to those skilled in the art from the following detailed description, together with the appended claims.

DETAILED DESCRIPTION OF THE PREFERRED EMBODIMENTS

The technical terminology with reference to biological, clinical, electronic, mathematical and statistical expressions used herein conform to conventionally accepted definitions.

The terms "sample" or "specimen" are interchangeably used herein and refer to biological material obtained from tissue, spinal fluid, bone marrow, blood, or other sources. A sample can also include viruses, bacteria, or other pathogens. A typical example of a biological specimen would be blood drawn from a subject. As utilized herein the term "cells" refers to animal or plant cells, cellular bacteria, fungi, which are identifiable separately or in aggregates. For example, cells can be human red blood cells (RBC) and white blood cell (WBC) populations, cancer, or other abnormal cells. The terms "target" or "target population" refers herein to biological entities of interest that may be present in a biological specimen that is being analyzed. A typical example of members of a target population would be CD4 positive cells in a blood sample. Conversely, the terms "non-target" or "non-target population" as used herein refer to entities present in a biological specimen, are not the subject of the analysis.

System Design

Figure 1:
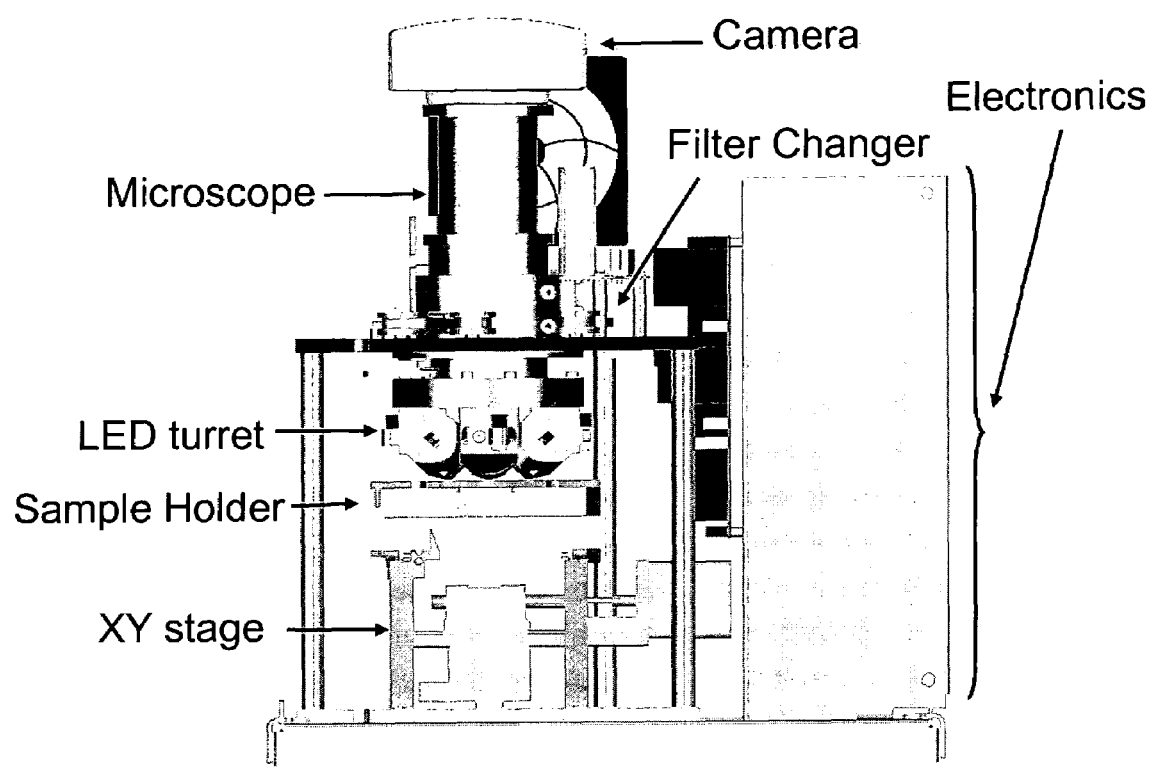
FIG. 1. Diagrammatic representation of relevant positioning of the device components in producing the compact structure of the device. The LED turret, filter changer, microscope and camera are positioned above the sample holder and XY stage which together are juxtaposed from the touchscreen and sample door as shown.

The different components of the apparatus (sometimes referred to herein by its project name, "EasyCount") are shown in FIG. 1. The imaging part of the apparatus is based on an epi-illumination fluorescence microscope. The surface of the sample chamber is illuminated by light emitting diodes. The light emitted from the fluorescently-labeled cells at the inner surface of the chamber is collected by an objective and focused onto a CCD.

To select and separate the target cells of interest, for example, from a whole blood sample, they are immunomagnetically labeled with a target specific antibody conjugated to magnetic particles, ferrofluids or superparamagnetic particles, as disclosed in U.S. Pat. Nos. 5,579,531 and 5,698,271 and U.S. application Ser. No. 10/208,939, each of which are incorporated by reference herein. The magnetic particles are typically about 180 nm in diameter and consist of a magnetic iron oxide core surrounded by a first polymeric layer to which streptavidin is conjugated. Target-specific antibodies can then be coupled to streptavidin by means of biotinylated antibodies. However, superparamagnetic particles made from other ferromagnetic materials, for example nickel, of similar or larger sizes of up to about 5 μm, can be similarly coated and used for magnetic labeling of target cells.

Finally alternative binders, such as lectins and boronate derivatives, recognizing glycosidic receptors on target cells may also be used in lieu of or in addition to antibodies on such magnetic capture particles.

For example, if the cells of interest are the total leukocyte population, a pan-leukocyte CD45 monoclonal antibody can be used that binds substantially specifically to all leukocyte populations in the blood sample. The cell labeling reaction can be conducted in test tubes or vials and an aliquot transferred to the sample chamber. Alternatively, the chamber itself can be used for incubations of specimen volumes of up to about 200 μl. The unbound non-magnetic materials are readily removable in the supernatants after magnetic separation. To enhance magnetic labeling efficiency of target cells one can use magnetic incubation or in-field incubation (PCT/US00/02034, which is incorporated by reference herein). To accomplish this, the sample is mixed with the magnetic ferrofluid in a test tube, and placed briefly inside a quadrupole high-gradient magnetic separator (HGMS) magnet (U.S. Pat. Nos. 5,186,827; 5,466,574; 5,641.072, incorporated by reference herein) after which it is removed from the magnet and remixed by vortexing. This step is repeated twice more. The quadrupole magnet delivers a radial magnetic gradient during the incubations, thus forcing the magnetic particles to move laterally as bead chains that sweep through the sample before accumulating at the wall surface. This multiple forced migration of magnetic particles increases the probability that the magnetic particles collide with or encounter the larger, substantially immobile, cells as compared to mere diffusional or Brownian collision of the magnetic particles and the target cells in the sample. Other magnetic configurations can be used that homogenously sweep through the sample.

Alternatively, samples assessed for cell viability by negative selection of dead cells. Total cell (live and dead) are stained with any agent known to stain cells (i.e. Thioflavin T). An identical sample is stained for only dead cells (i.e. ethidium bromide). The groups are counted and the difference gives a value for the total number of live cells. A modified microscope slide having a sealed viewing chamber, formed with a glass cover slip bonded to the surface of the slide. A chamber is formed between the cover slip and slide by molding a shape to allow partitioning of the fluid sample between an entry port and exit port. The total volume must accept a sample from a 10 ul pipette tip.

Sample Chamber and Magnet Holder for Immunomagnetic Enrichment and Observation

When a biological specimen is to be visually analyzed, it is necessary for the target population to be adjacent to the observation surface. This allows the optical arrangement to clearly focus on the target population in order to provide an accurate analysis. Once the members of the target population have been magnetically labeled, they can be manipulated to the observation surface for visual analysis.

Figure 3:
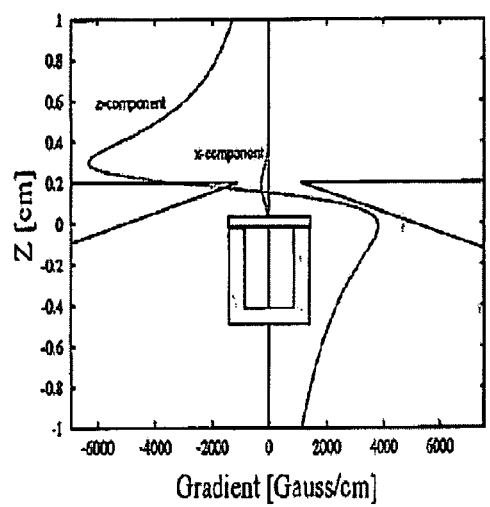
FIG. 3: (A) Magnetic gradient in the chamber in x- and z-direction. The x-component of the gradient is negligible. (B) Magnetically labeled white blood cells move upwards in the chamber, while unlabelled red blood cells move downwards.
Figure 3:
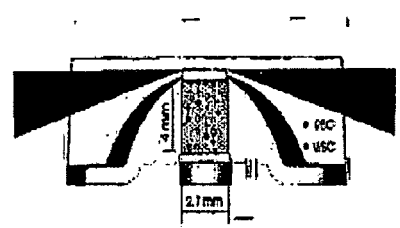

The chamber and the magnetic yoke holder have been previously described (U.S. Pat. Nos. 5,985,153; 6,136,182; PCT/US02/04124, which are each incorporated by reference herein). The chamber consists of a molded body of inner dimensions 30×2.7×4 mm, length×width×height respectively. It has an optically transparent planar top surface) that is sealable, if required, by means of a removable plug cap. The sample chamber is shown (FIG. 3) oriented in the horizontal plane for probing with a vertical light beam. However, an alternative instrument design would accommodate an uncapped detection chamber or other suitable sample cuvet with the magnetic holder oriented vertically and the light beam oriented horizontally.

The magnetic chamber holder or yoke is designed such that the chamber is positioned 2 mm below the top of two magnetic pole pieces. The pole pieces are made of Neodymium Iron Boron alloy with an internal magnetization of 13,700 Gauss (Crumax Magnetics Inc, Elizabethtown, KT). The two pieces are mounted to form a 3 mm gap between their faces that are an angled 70° relative to the z-axis. This arrangement, depicted in FIGS. 3A and B, creates a magnetic gradient inside the chamber, which is pointing in the z-direction and has a negligible component in the x-direction. Therefore, the immunomagnetically-labeled cells and unbound ferrofluid particles move in the vertical direction to the upper surface. The imaged surface area correlates directly with the volume fraction underneath the imaged area (FIG. 3B). To obtain a representative and accurate number of cells per unit volume, it is important that the cells are uniformly distributed and immobilized over the viewing surface, which requires that the magnetic field conditions also are uniform over the full area of the glass surface.

A further improvement to the magnetic arrangement described above was to "spring load" the yoke assembly. This positions each sample cartridge into a repeatable location. Because of this, the specimens that are being analyzed are always in focus in the Z-axis as they are being imaged. This is extremely important for using the apparatus of the invention as a fast analyzer because independent focusing for each sample cartridge is no longer necessary. As the sample cartridges are manufactured with precision, the yoke assembly can position every sample to always be in focus.

Figure 4:
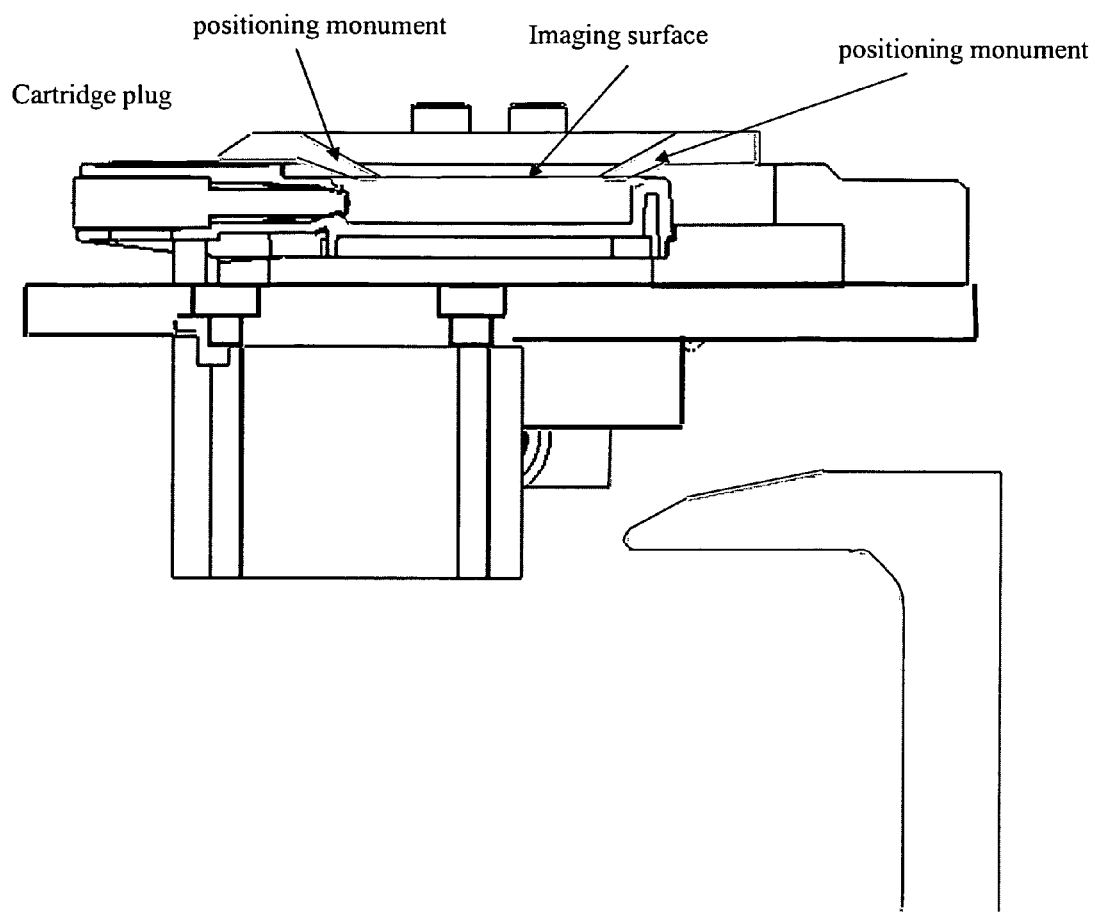
FIG. 4: A cross-sectional representation of the improved magnetic cartridge holder mounted on observation stage. The "spring positioning" tabs are positioned along the longitudinal axis as shown.

Thus, the system is further improved to include spring loaded clips to hold the chamber against the upper surface of the yoke assembly (FIG. 4). This modification removes variations in the manufacture of multiple assemblies. Accordingly, the viewing surface is consistently held in the same z-axis for observation. Any variation in the production of the assemblies is reflected on the lower portion of the yolk and does not affect the Z-axis for imaging. Thus for cell focus, no active z-stage is required as variations in yolk tolerance between is expressed on the bottom surface of the yolk.

A similar design for the modified microscope slide holder provides for no variation in the z-axis. Here, the same principle provides a "spring load" affect on the microscope slide, eliminating focusing the Z-axis.

The Imaging System

Fluorescent Staining of Leukocytes

In order to make the nucleated cells detectable, the sample is stained with acridine orange (AO; Molecular Probes, Inc., Eugene, Oreg.), a vital dye that stains the nucleus of live cells as well as several constituents of the cytoplasm. Acridine orange has its absorption peak at 490 nm, and emits at 520 nm when bound to DNA. Other fluorescent dyes, such as Hoechst 33258, and Hoechst 33342 may be used. In general, any fluorescent dye that non-specifically stains cells, cytoplasm, cellular nucleic material, or the nucleus itself can be used. These dyes are referred to herein as "non-specific fluorescent dyes." Also, any particle that can be attached to an antibody and detected by microscopy is considered in the present invention.

In general, illumination in fluorescence microscopy is achieved by mercury arc or quartz-halogen lamps. In some microscopy systems, more expensive lasers are used for illumination. However, recent advances in semiconductor technology have lead to the development of high-brightness light emitting diodes that can compete with incandescent light sources and lasers. The advantages of using LEDs as light source are that they are relatively compact, inexpensive, and have a long lifetime without a need to replace. The spectral power distribution of a LED is fairly narrow, with half-bandwidths of about 20 to 50 nm, depending upon the substrate material. LEDs produce highly saturated, nearly monochromatic light and are ideal for constructing the compact and inexpensive cytometer devices of this invention.

Optics

Figure 2:
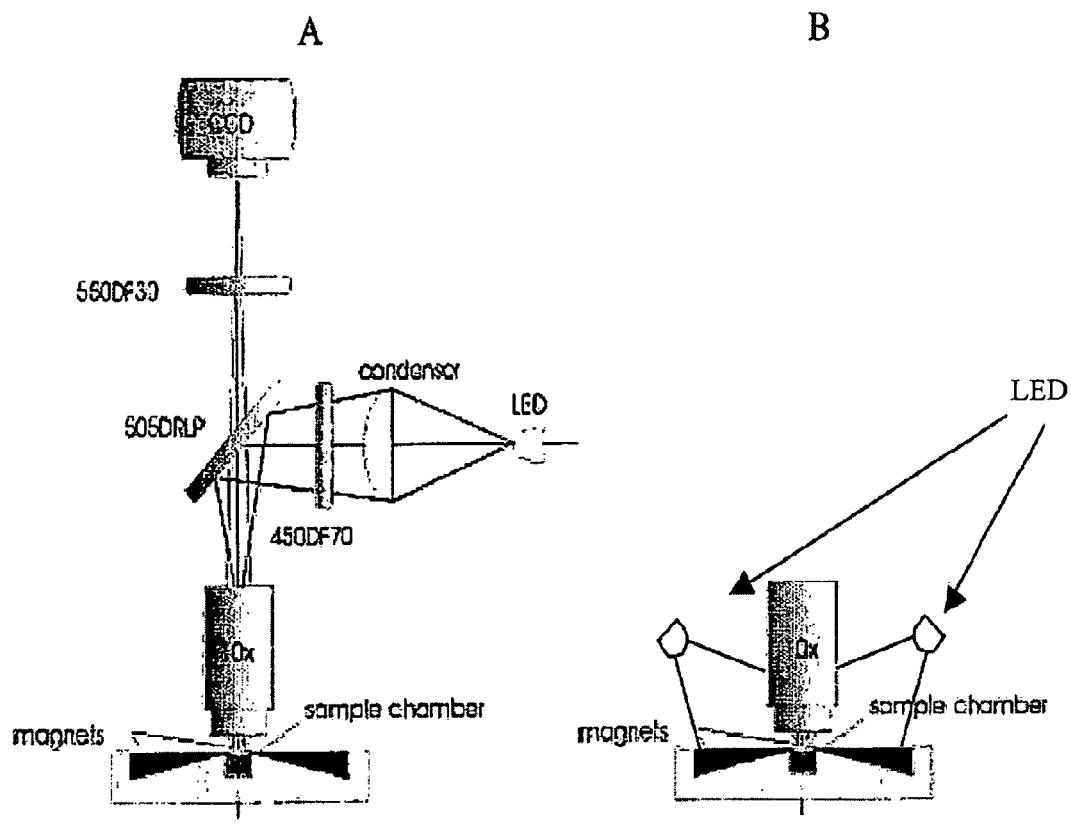
FIG. 2: Schematic representations of optical and illumination arrangements. In (A), light from an LED is focused on the sample through a condenser, a set of filters and a 10× objective. An image of the fluorescence of the cells is projected on and captured by a CCD camera. In (B), the light of two LED's is directly projected onto the sample.

The light from an LED is collected by a condenser lens with a focal distance of 27 mm, passes a short pass optical filter, focused at the sample plane. This optical configuration results in a homogeneous illumination of the sample area. The light emitted from the fluorescent cells collected at the underside of the glass surface of the chamber is collected by the objective (1-20×, NA 0.03-0.25), after which it is filtered by a band-pass or long pass filter and focused onto a high QE, high bit resolution (minimum 12 bits) CCD camera (DSI, Meade Instruments Corporation, Irvine, Calif.). FIG. 2A shows the conventional epi-illumination mode. FIG. 2B shows a direct side illumination of the viewing surface with one or more LEDs in a "floodlight" arrangement, which provides sufficient excitation energy, and may be a simpler and less expensive illumination mode.

Figure 5:
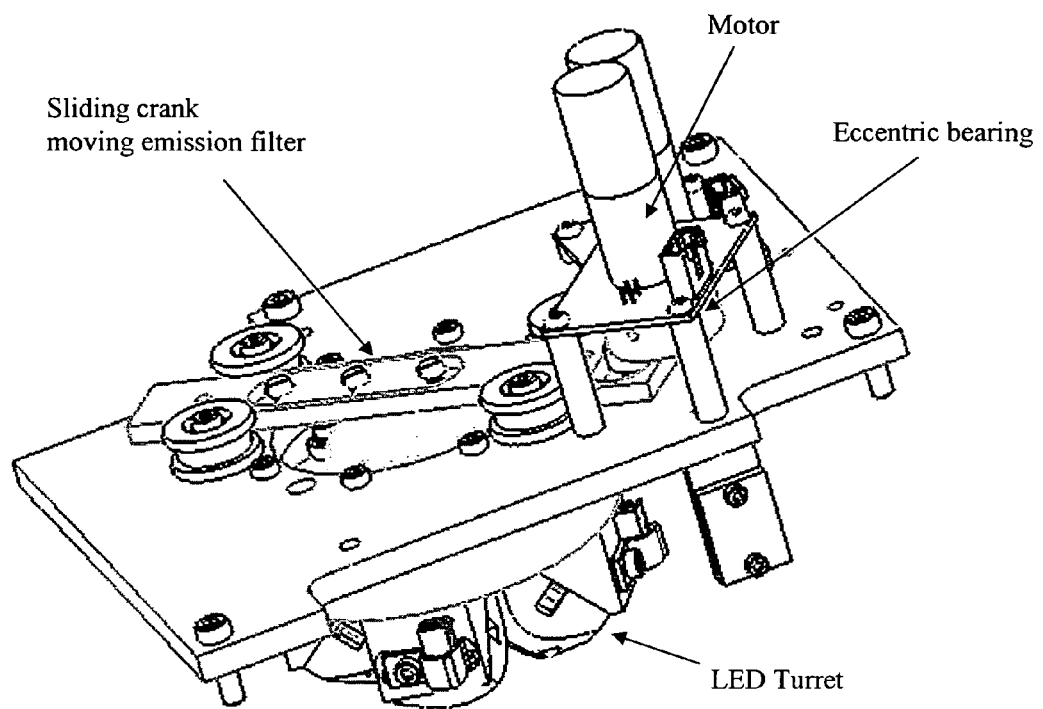
FIG. 5: Representation of the filter changer. An eccentric bearing positions the sliding crank, having two or more filters, in position with the light path. Microscope is removed.

The present invention improves upon the orientation of the LED with respect to the cartridge and the cell alignment. LED's are aligned along the longitudinal axis of the cartridge, ensuring maximum light intensity. FIG. 4 depicts the advantage of orientating the components in a small area using a fixed distance between the specimen and objective lens In addition, the present invention improves upon the positioning of the filter assembly. FIG. 5 shows a general orientation of the emission filter set positioned in EasyCount. The filter changer is a sliding crank with an eccentric bearing to position the filter. This orientation provides for an inexpensive and compact device for switching between two or more filters.

Camera

The CCD used in this set-up (DSI, Meade Instruments Corporation, Irvine, Calif.) where the image is retrieved from the camera by software and stored in a computer memory as 12/16-bit TIF images.

Image Processing and Analysis

Algorithms were developed to count the cells in the images obtained from the optical system. First, a model is presented to describe the cell images. Then, a method for spot detection in the images is introduced. Cells are enumerated based on size, intensity, uniformity, aspect ration, etc.

EXAMPLE 1

Cell enumeration is commonly performed using expensive flow cytometry (FC) or less accurate manual count methods. Here, we present an automated microscope device to obtain absolute cell counts based on fluorescence with cell identification not prone to operator to operator variability of manual cell counts.

The device of the present invention, EasyCount (EC), is a simple fluorescence microscope coupled to an on board microcomputer. It has a 5× objective (NA 0.1) and 4 high power LEDs for excitation at two different wavelengths. Each LED is equipped with an excitation filter and a collection lens for the stray light. The LEDs are placed next to the objective lens and illuminates the sample directly. Available illumination wavelengths are 490, 530 and 590 nm. Detection is performed by capturing a fluorescent image from a field of view of 0.95×1.3 mm on a 16 bit camera. The light is collected by the objective and selected by emission filters. The illumination and detection wavelengths can be set-up for acridine orange, ethidium bromide, phycoerithrin and allophycocyanin. The enumeration of cells takes place after image analysis by the algorithm. Analysis time for a sample with two dyes on a single location is <2 minutes. The sample can be introduced using a sample holder for a microscope slide configuration or MagNest®. Scanning multiple fields on a sample is allowed by a 2 axis stage with 25 micron positioning accuracy. The overall instrument dimensions are 30×30×35 cm.

Sensitivity (signal to noise ration; SNR) was tested using 8 micron beads with a known number of molecules of allophycocyanin and fluorescence microscope (1×, NA 0.45).

TABLE 2

Comparison of SNR performance between EC and FM

| Acquisition time | #APC molecules | Negative control | 25k | 50k | 85k | 260k | 800k |
|---|---|---|---|---|---|---|---|
| 2.8 s | SNR EC | 4 | 18 | 25 | 51 | 78 * | 141 * |
| 0.1 s | SNR FM | 0 | 18 | 27 | 73 | 173 | 357 |

* signal from beads saturated the camera, SNR not accurate due to saturation

The dynamic range of enumeration was tested with acridine orange stained PC3-9 cells and with a well depth of 0.15 mm, the dynamic range was found to be $3.10^4$ to $1.10^7$ cells/ml. Using ferromagnetic enrichment and multiple field imaging, the lower limit of detection can be extended to approximately 200 cells/ml.

The EasyCount system is a cost effective bench top cell enumerating system. It has a flexible optical design and a sensitivity and dynamic range sufficient for a wide range of cell counting applications.

EXAMPLE 2

Cells from the prostate cell line PC3-9 were harvested and resuspended in RPMI culture media. Cell count and viability determination by hemacytometer involved mixing cells 1:1 with trypan blue. Cells to be counted on EasyCount were mixed 1:1 with a cocktail containing acridine orange and ethidium bromide. Samples were then loaded onto the ViaSure™ slide, placed on the EasyCount platform, and viable and non-viable counts were obtained. Cells at concentrations ranging from $2\times10^4$/ml through $5\times10^6$/ml were analyzed for total cell counts using both the hemacytometer and EasyCount. Regression analysis of the data showed an $R^2$ of 0.999 with a slope of 1.2. At the upper end of the titration curve, hemacytometer counts required an additional dilution step which was not necessary with EasyCount. Regression analysis of the EasyCount assay linearity showed an $R^2$ of 0.97 with a slope of 0.99. Correlation of sample viability involved making mixtures of cells with viabilities of approximately 0, 25, 50, 75, and 100%. Non-viable cells were prepared by permeabilization. Regression analysis of the data showed an $R^2$ of 0.999 with a slope of 0.977. Precision data for the hemacytometer and EasyCount using ten replicates showed a mean cell concentration, standard deviation, and CV of $0.975\times10^6$/ml, $1.49\times10^5$/ml, 15.3% and $1.036\times10^6$/ml, $1.56\times10^5$/ml, 15.1% respectively.

EXAMPLE 3

Counting residual leukocytes in leukodepleted blood products is done using either a specialized hemacytometer (Nageotte) or by flow cytometry on nucleic acid-stained samples. Nageotte counting is tedious and labor-intensive. Flow cytometry requires expensive instrumentation, a skilled operator, and has low sample throughput. The fluorescent imaging system of the present invention is useful for counting low numbers of residual leukocytes in leukodepleted blood products.

One hundred microliters of blood were mixed with anti-CD45-ferrofluid and a fluorescent stain to visualize the cells. A variety of fluorescents stains were evaluated among which nucleated acid dyes and anti-CD45-PE. Leukocytes were magnetically mounted in a CellTracks® cartridge and MagNest® and imaged using either an EasyCount Cell Counter or a fluorescent microscope. The number of leukocytes present was also measured by flow cytometry (BD LeukoCount) and by Nageotte chamber.

Using ACD whole blood samples, mean leukocyte counts were similar in EasyCount and Nageotte chamber (91 cells/uL vs. 94 cells/uL, n=31). EasyCount and Nageotte methods were linear at counts below 250 cells/uL ($R^2$=0.9948). EasyCount precision at 38 cells/uL (range=27-52 cells/uL, 27 replicates) was 15%. Both EasyCount and Nageotte cell counts were more sensitive than flow cytometry (means=73, 63, and 24 cells/uL, respectively, n=11). When EasyCount was used to test segments from leukocyte reduced blood bags, 163/185 samples were leukocyte negative, 21 had 1-15 leukocytes/uL, and one contained 2,629 cells/uL. Unexpectedly, 30% of the leukocyte negative samples contained non-cellular clumps stained that stained brighter with acridine orange and other nucleic acid dyes tested than the leukocytes. Staining with anti-fibrin FITC demonstrated that these clumps consisted of fibrin. However, we were able to count only CD45 captured leukocytes, without interference from fibrin, by staining cells with CD45-PE recognizing a different CD45 epitope than those used for magnetic capture.

EXAMPLE 4

With image cytometry such as in EasyCount, cells are usually randomly distributed on the analysis surface. To reduce imaging times, a PDMS (poly-dimethyl siloxane) microstructures were developed to align the cells in pre-defined areas and at the same time offer unobstructed imaging of the cells (as described in WO 06061075). These microstructures are produced by making PDMS molds of etched silicon wafers. The unique properties of PDMS make it an excellent material to use for these microstructures. It is optically transparent down to 300 nm, can easily be glued to supporting structures and is cost effective. Furthermore, structures can be replicated with sub-micron accuracy and adhesion of cells to the material is low.

Figure 6:
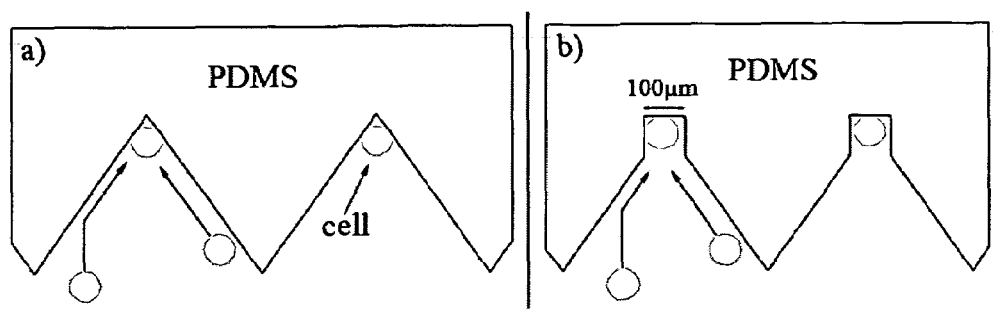
FIG. 6: Overview drawings of a) V-Groove- and b) Foxhole microstructures made on a PDMS template. Shown is the position of the cell to be imaged.

To align the cells, a force is needed; e.g. gravity or a magnetic force. The latter is used in the CellTracks® system, a Circulating Tumor Cell analysis system, to align cells in the microstructures. Characterization of these cells is done by scanning them with 4 homogenized laserspots. Essential properties of two microstructures like alignment and image quality were investigated using SKBR3 cells. They were immuno-magnetically labeled and aligned in the structures by a magnetic field. FIG. 6 gives an overview drawing of the two microstructures.

The first structure arranges the cells in a long line, like in Flow Cytometry, and is suited for cell counting. Cells are illuminated and imaged from the top of the structures shown in the figure. Image quality in the V-Groove is reduced by light diffraction at the tip of the V-Groove. The image quality is improved in the Foxhole structure were the cells are concentrated at a flat surface. Alignment efficiency of both structures is greater than 97%. Array orientation (2D grid) is also possible (not shown in figure) in square and hexagonal packing.

The V-Groove offers excellent alignment and good quantitative properties. The Foxhole microstructure offers good alignment and excellent image quality. It allows the illumination area to be matched to the channel width in the Cell-Tracks system, thereby reducing scanning times by a factor of 3.

While certain of the preferred embodiments of the present invention have been described and specifically exemplified above, it si not intended that the invention be limited to such embodiments. Various modification may be made thereto without departing from the spirit of the present invention, the full scope of the improvements are delineated in the following claims.

What we claim is:

1. An improvement upon an apparatus for detecting and enumerating a target population within a biological specimen having an illumination means, means for acquiring an image, a magnetic arrangement capable of receiving a sample chamber containing said biological specimen, said magnet arrangement further being capable of allowing said sample chamber to be illuminated and imaged, a processor, and an output means, said improvement comprising:
    a) filter changing means having sliding crank means for positioning said filters along a light path;
    b) said illumination means of one or more light emitting diodes aligned along the longitudinal axis of a sample chamber; and
    c) support means having an arrangement of spring loaded monuments for maintaining an imaging surface along a z-axis position wherein said support means provide a fixed distance between a cell and objective lens.

2. The apparatus of claim 1, wherein said processor determines the number CD45 positive target cells in the sample.

3. The apparatus of claim 2, wherein said output means provides a measure of leukodepletion.

4. An apparatus for detecting and enumerating a target population within a biological specimen, said apparatus comprising:
    a) an illumination means;
    b) a means for acquiring an image;
    c) a modified microscope slide having a viewing chamber with an inlet port and exit port, wherein said chamber allows for individual target enumeration;
    d) a processor for performing one or more analytical algorithms on said image; and
    e) an output means.

5. The apparatus of claim 4, wherein said microscope slide is positioned on an arrangement of spring loaded monuments for maintaining an imaging surface along a z-axis position.

6. The apparatus of claim 4, wherein said processor determines the number of live and dead target cells in the sample.

7. The apparatus of claim 5, wherein said output means provides a measure of target cell viability.

* * * * *